(12) United States Patent
Hayes et al.

(10) Patent No.: US 9,603,802 B2
(45) Date of Patent: Mar. 28, 2017

(54) EXTRUSION

(75) Inventors: Geoffrey Gerard Hayes, Saffron Walden (GB); Vincenzo Martinelli, Cambridge (GB); Hassan Mohammad, Ely (GB); Derek Allan Prater, Milton (GB); Harjit Tamber, Hitchin (GB); Malcolm Walden, Hardwick (GB); Steve Whitelock, Milton (GB)

(73) Assignee: Euro-Celtique S.A., Luxembourg (LU)

( * ) Notice: Subject to any disclaimer, the term of this patent is extended or adjusted under 35 U.S.C. 154(b) by 0 days.

(21) Appl. No.: 12/241,650

(22) Filed: Sep. 30, 2008

(65) Prior Publication Data

US 2009/0029170 A1    Jan. 29, 2009

Related U.S. Application Data

(63) Continuation of application No. 11/056,035, filed on Feb. 11, 2005, now abandoned.

(30) Foreign Application Priority Data

Feb. 12, 2004  (GB) .................................. 0403098.7

(51) Int. Cl.
*A61K 9/16*    (2006.01)

(52) U.S. Cl.
CPC .............. *A61K 9/1635* (2013.01); *A61K 9/16* (2013.01); *A61K 9/1694* (2013.01); *Y10T 428/2982* (2015.01)

(58) Field of Classification Search
CPC .................................. A61K 9/16; A61K 9/1694
USPC .. 264/141, 142, 145, 148, 151, 152, 173.12, 264/173.16, 464, 45.9, 46.1, 623, 634, 264/638
See application file for complete search history.

(56) References Cited

U.S. PATENT DOCUMENTS

| 4,080,134 A | * | 3/1978 | Klaeysen et al. ............. 425/143 |
| 4,242,219 A | | 12/1980 | Bogerman et al. |
| 4,327,050 A | | 4/1982 | Salmon |

(Continued)

FOREIGN PATENT DOCUMENTS

| EP | 0 465 338 A1 | 1/1992 |
| EP | 0 665 010 A1 | 8/1995 |

(Continued)

OTHER PUBLICATIONS

Amighi, K., and Moës, A.J., "Evaluation of thermal and film forming properties of acrylic aqueous polymer dispersion blends: Application to the formulation of sustained-release film coated theophylline pellets," *Drug Development and Industrial Pharmacy* 21 (20): 2355-2369, Marcel Dekker, Inc., United States (1995).

(Continued)

*Primary Examiner* — Stella Yi
(74) *Attorney, Agent, or Firm* — Sterne, Kessler, Goldstein & Fox P.L.L.C.

(57) ABSTRACT

The invention relates to a process for preparing a controlled release pharmaceutical extrudate using a melt extruder, wherein the melt extruder comprises a die-head supporting a die-plate in which orifices are located, and a cutter adjacent to the die-head, and wherein the cutter cuts the extruded mix as it emerges under pressure and still molten or softened from the orifices of the die-plate.

5 Claims, 5 Drawing Sheets

(56) References Cited

U.S. PATENT DOCUMENTS

| | | | |
|---|---|---|---|
| 4,331,623 A * | 5/1982 | Zurkoff et al. | 264/141 |
| 4,801,460 A * | 1/1989 | Goertz et al. | 514/772.5 |
| 4,948,615 A * | 8/1990 | Zallie et al. | 426/578 |
| 5,085,815 A | 2/1992 | Yeh et al. | |
| 5,290,560 A | 3/1994 | Autant et al. | |
| 5,552,159 A * | 9/1996 | Mueller et al. | 424/464 |
| 5,762,975 A * | 6/1998 | Rockstedt | 425/186 |
| 5,945,127 A * | 8/1999 | Breitenbach et al. | 424/489 |
| 5,958,452 A * | 9/1999 | Oshlack et al. | 424/457 |
| 5,965,161 A | 10/1999 | Oshlack et al. | |
| 6,063,821 A | 5/2000 | Breitenbach et al. | |
| 6,190,591 B1 * | 2/2001 | van Lengerich | A23L 1/0023 264/141 |
| 6,290,990 B1 * | 9/2001 | Grabowski et al. | 424/499 |
| 6,509,038 B2 | 1/2003 | Baert et al. | |
| 7,572,463 B2 | 8/2009 | Bartholomaeus et al. | |
| 8,920,836 B2 | 12/2014 | Hayes et al. | |
| 2001/0007678 A1 | 7/2001 | Baert et al. | |
| 2001/0018063 A1 * | 8/2001 | Cummings et al. | 424/405 |
| 2001/0033865 A1 | 10/2001 | Oshlack et al. | |
| 2001/0038852 A1 | 11/2001 | Kolter et al. | |
| 2002/0010127 A1 | 1/2002 | Oshlack et al. | |
| 2003/0026839 A1 * | 2/2003 | Oshlack et al. | 424/469 |
| 2003/0044458 A1 | 3/2003 | Wright, IV et al. | |
| 2003/0091698 A1 * | 5/2003 | Marsland | 426/94 |
| 2004/0170680 A1 | 9/2004 | Oshlack et al. | |
| 2006/0165790 A1 | 7/2006 | Walden et al. | |
| 2007/0259045 A1 | 11/2007 | Mannion et al. | |
| 2007/0298103 A1 | 12/2007 | Hayes | |
| 2009/0148517 A1 | 6/2009 | Oshlack et al. | |
| 2010/0172974 A1 | 7/2010 | Oshlack et al. | |
| 2011/0104214 A1 | 5/2011 | Oshlack et al. | |
| 2012/0141583 A1 | 6/2012 | Mannion et al. | |

FOREIGN PATENT DOCUMENTS

| | | |
|---|---|---|
| EP | 1 348 429 A2 | 10/2003 |
| EP | 1 889 621 A1 | 2/2008 |
| JP | 59096187 * | 2/1984 |
| JP | 03076721 * | 2/1991 |
| WO | WO 88/03795 | 6/1988 |
| WO | WO 92/10173 | 6/1992 |
| WO | 93/10765 | 6/1993 |
| WO | 96/14058 | 5/1996 |
| WO | WO 98/18610 A1 | 5/1998 |
| WO | WO 00/13687 | 3/2000 |
| WO | WO 01/15667 A1 | 3/2001 |
| WO | WO 02/058677 A1 | 8/2002 |
| WO | 02/087512 | 11/2002 |
| WO | WO 03/004009 A1 | 1/2003 |
| WO | 03/013433 | 2/2003 |
| WO | WO 03/84504 | 10/2003 |
| WO | WO 2005/000310 A1 | 1/2005 |
| WO | WO 2005/079760 A1 | 9/2005 |

OTHER PUBLICATIONS

BASF website: "Kollidon® SR Technical Information," pp. 1-12 (Jul. 2007).

Bauer, K.H., et al., "Coated Pharmaceutical Dosage Forms: Fundamentals, Manufacturing Techniques, Biopharmaceutical Aspects, Test Methods and Raw Materials," p. 92, CRC Press, United States (1998).

Degussa website/Pharma Polymers, "Pharmacopoeial Monographs and Drug Master Files," pp. 1-4 (Jun. 2004).

Degussa website/Pharma Polymers, "Products & Services," pp. 1-12 (Jan. 2005).

Degussa website, "Ibuprofene Sustained Release Matrix Tablets: Application of EUDRAGIT® NE 30 D," pp. 1-3 (Feb. 2002).

Degussa website, "Specifications and test methods for EUDRAGIT® NE 30 D," pp. 1-4 (Sep. 2004).

EVONIK Industries website: "Specifications and test methods for EUDRAGIT® NE 30 D," pp. 1-4 (Sep. 2007).

EVONIK Industries website: "Specifications and test methods for EUDRAGIT® NE 40 D," pp. 1-4 (Nov. 2007).

EVONIK Industries website: "Specifications and test methods for EUDRAGIT® NE 30 D," pp. 1-4 (Nov. 2007).

Sood, A., et al., "Use of Extrusion—Spheronization to Develop Controlled-Release Dosage Forms for Diltiazem Hydrochloride," *Pharmaceutical Technology*, p. 62-85, Advanstar Communications, United States (Apr. 2004).

Wurster, D.E. et al., "Effect of Curing on Water Diffusivities in Acrylate Free Films as Measured via a Sorption Technique," *AAPS PharmSciTech 8(3) Article 71:E1-E6*, American Association of Pharmaceutical Scientists, United States (Aug. 2007).

International Search Report for International Application No. PCT/GB2005/050014, European Patent Office, Netherlands, mailed Aug. 4, 2005.

International Preliminary Report on Patentability for International Application No. PCT/GB2005/050014, European Patent Office, Netherlands, issued Aug. 14, 2006.

Office Action mailed Aug. 3, 2009, in U.S. Appl. No. 10/588,978, Hayes, G.G., having a 35 U.S.C. 371(c) date of Apr. 24, 2007.

Office Action mailed May 14, 2010, in U.S. Appl. No. 10/588,978, Hayes, G.G., having a 35 U.S.C. 371(c) date of Apr. 24, 2007.

Office Action mailed Jan. 21, 2011, in U.S. Appl. No. 10/588,978, Hayes, G.G., having a 35 U.S.C. 371(c) date of Apr. 24, 2007.

Office Action mailed Jan. 20, 2012, in U.S. Appl. No. 10/588,978, Hayes, G.G., having a 35 U.S.C. 371(c) date of Apr. 24, 2007.

Office Action mailed Oct. 2, 2012, in U.S. Appl. No. 10/588,978, Hayes, G.G., having a 35 U.S.C. 371(c) date of Apr. 24, 2007.

Office Action mailed Jun. 4, 2013, in U.S. Appl. No. 10/588,978, Hayes, G.G., having a 35 U.S.C. 371(c) date of Apr. 24, 2007.

Non-Final Office Action mailed Mar. 21, 2014 in U.S. Appl. No. 10/588,978, inventors Hayes et al., 371(c) date Apr. 24, 2007.

EVONIK Industries website: "Specifications and test methods for EUDRAGIT® NE 30 D" Oct. 2011, 5 pages.

EVONIK Industries website: "Specifications and test methods for EUDRAGIT® NE 40 D" Oct. 2011, 5 pages.

EVONIK Industries website: "Specifications and test methods for EUDRAGIT® NM 30 D" Oct. 2011, 5 pages.

EVONIK Industries website, "EUDRAGIT® RS PO—Targeted Drug Release and Tailored Service," accessed at http://eudragit.evonik.com/product/eudragit/en/products-services/eudragit-products/sustained-release-formulations/rs-po/pages/default.aspx, accessed on Dec. 9, 2014, 2 pages.

Notice of Allowance mailed Aug. 19, 2014, in U.S. Appl. No. 10/588,978, inventors Hayes, G., et al., having a §371(c) date of Apr. 24, 2007.

European Search Report for European Patent Application No. EP 05 07 5341, European Patent Office, Rijswijk, Netherlands, mailed on Mar. 3, 2011.

* cited by examiner

EXTRUSION

CROSS-REFERENCE TO RELATED APPLICATIONS

This application is a continuation of U.S. application Ser. No. 11/056,035, filed Feb. 11, 2005, which claims the benefit of Great Britain Application No. 0403098.7, filed Feb. 12, 2004, the disclosures of which are incorporated by reference herein in their entireties.

The present invention relates to extrusion, and in particular to melt extrusion of multiparticulates which provide controlled release of an active ingredient.

BACKGROUND OF THE INVENTION

Multiparticulates of uniform dimensions with modified drug release properties can readily be manufactured by melt extrusion technology. Melt extrusion is a solvent-free single-step process for manufacturing multiparticulates and is particularly useful for drug release modification. By selection of suitable polymers and additives, melt extrusion technology can be used both to enhance the solubility, and subsequently the bioavailability, of poorly water soluble drugs as well as to retard drug release of moderate to highly water soluble drugs for controlled release products.

The backbone of melt extrusion technology is the application of thermoplastic materials which act as binders for embedded drugs in solution or dispersion form within the matrix. Thermoplastic polymers with low glass transition temperatures (Tg) are preferred for processing by melt extrusion. Lower processing temperatures are also preferred with respect to the stability of heat sensitive drugs and other necessary excipients. Polymer glass transition temperatures can also be further reduced to facilitate processing at lower temperature with optional addition of plasticisers.

WO 9614058 provides a sustained-release pharmaceutical formulation, comprising a melt-extruded blend of a therapeutically active agent, one or more materials selected from the group consisting of alkylcelluloses, acrylic and methacrylic acid polymers and copolymers, shellac, zein, hydrogenated castor oil, hydrogenated vegetable oil, and mixtures thereof; and one or more hydrophobic fusible carriers which provide a further retardant effect and are selected from the group consisting of natural or synthetic waxes, fatty acids, fatty alcohols, and mixtures thereof, the fusible carrier having a melting point from 30 to 200° C. The melt-extruded blend is divided into a unit dose containing an effective amount of said therapeutically active agent to render a desired therapeutic effect and providing a sustained-release of said therapeutically active agent for a time period of from about 8 to about 24 hours.

Furthermore, WO 9614058 describes a method of preparing a sustained-release pharmaceutical extrudate suitable for oral administration. The method comprises:

blending a therapeutically active agent together with (1) a material selected from the group consisting of alkylcelluloses, acrylic and methacrylic acid polymers and copolymers, shellac, zein, hydrogenated castor oil, hydrogenated vegetable oil, and mixtures thereof and (2) a fusible carrier selected from the group consisting of natural or synthetic waxes, fatty acids, fatty alcohols, and mixtures thereof; said retardant material having a melting point between 30-200° C. and being included in an amount sufficient to further slow the release of the therapeutically active agent;

heating said blend to a temperature sufficient to soften the mixture sufficiently to extrude the same;

extruding said heated mixture as a strand having a diameter of from 0.1-3 mm;

cooling said strand; and dividing said strand to form non-spheroidal multi-particulates of said extrudate having a length from 0.1-5 mm; and dividing said non-spheroidal multi-particulates into unit doses containing an effective amount of said therapeutically active agent, said unit dose providing a sustained-release of said therapeutically active agent for a time period of from about 8 to about 24 hours.

Thus, in practice, the stranded extrudate is congealed on a conveyor belt and cut into pellets. Such pellets typically have a cylindrical shape.

SUMMARY OF THE INVENTION

According to the present invention, we provide a process for preparing a controlled release pharmaceutical extrudate, wherein a cutter cuts the extruded mix as it emerges under pressure and still molten from the orifices of the die-plate.

The cutter is suitably a rotary cutter with one or more blades which sweep over the surface of the die-head to pass the orifices. Two diametrically opposed blades are preferred. Ideally, the outer surface of the die-head is coated with a non-stick material, e.g. polytetrafluoroethylene (PTFE). As the cut extrudate multiparticulates expand and cool, they tend to form rounded surfaces. By appropriate adjustment of the rate of extrusion and the speed of the cutter blade, as well as generally cylindrical multiparticulates, it is possible for example to arrange for spherical or substantially spherical, ellipsoidal or disc shaped multiparticulates to be obtained. In one embodiment a stream of air is directed into the region of the surface of the die-head, the air being at a reduced temperature to cool the extrudate and to speed solidification.

Spherical multiparticulates produced by this method offer a number of advantages:

Better batch to batch reproducibility.
Easier coating and lower coating weight required.
Better capsule filling and higher yield.
More stable at elevated temperature.
More tamper resistant.
Reduce or eliminate some problems that arise during conveying and pelletising the strands such as strands fracturing to different length pellets and possible static charge.

Our preferred compositions include a water insoluble ammonium methacrylate copolymer. The insoluble ammonium methacrylate copolymer is suitably Eudragit RS PO, which is an ammonium methacrylate copolymer. In particular, Eudragit RS PO is a sparingly water permeable thermoplastic polymer which can significantly retard release of embedded oxycodone in its matrix. The insoluble ammonium methacrylate copolymer can form all or part of the release controlling material employed in the extrusion method.

A further preferred polymer which can form part of the release controlling material is a neutral poly(ethyl acrylate, methyl methacrylate) copolymer. Neutral poly(ethyl acrylate, methyl methacrylate) copolymer is commercially available in the form of an aqueous dispersion. Two products, Eudragit NE 30 D and Eudragit NE 40 D, comprise respectively 30% and 40% of the polymer. These products are used conventionally in the preparation of controlled release coats.

We now find that by utilising a neutral poly(ethyl acrylate, methyl methacrylate) copolymer in the preparation of controlled release pharmaceutical extrudates, we can obtain melt extruded multiparticulates which exhibit rubber-like characteristics. Such rubbery extrudates can exhibit enhanced resistance to tamper. In particular, it appears that the rubbery characteristics are imparted by the step of melt extrusion. Tamper resistance is of special importance for products containing opioid analgesics or other active ingredients which are subject to abuse.

The neutral poly(ethyl acrylate, methyl methacrylate) copolymer is suitably employed in an amount by weight of up to 66% in the mix for extrusion, say 20 to 66% of the extrusion mix, more typically from 20 to 50%, such as 30 to 40% of the extrusion mix.

The neutral poly(ethyl acrylate, methyl methacrylate) can be employed with other ingredients including a drug or other active ingredient.

A plasticiser and/or a lubricant is preferred when using an extruder with a relatively low torque capability such as a Leistritz Micro 18 machine. With a larger extruder, such as a Leistritz Micro 27, similar formulations, without or with relatively low levels of plasticiser and/or lubricant, may be processed.

The plasticiser is normally chosen from water insoluble solids such as cetyl alcohol, stearyl alcohol and cetostearyl alcohol; water soluble solids such as sorbitol and sucrose and high molecular weight polyethylene glycol, water insoluble liquids such as dibutyl sebacate and tributyl citrate and water soluble liquids such as triethyl citrate, propylene glycol and low molecular weight polyethylene glycol. Stearyl alcohol is a preferred plasticiser. Another preferred plasticiser is a high molecular weight polyethylene glycol of MW 1000 to 20000, such as PEG 6000.

A lubricant can be included. The lubricant is normally a solid at room temperature, and is suitably chosen from stearic acid, glycerol dibehenate, magnesium stearate, calcium stearate, talc and silicone dioxide (fused silica). The presence of lubricant in the melt extrusion formulation improves blending, kneading and conveying and reduces cohesion and adhesion forces. Smooth extrusion at low to moderate temperatures improves batch to batch reproducibility and reduces the strain on both the product and equipment. Stearic acid, possibly in the form of a salt, is a preferred lubricant. Another preferred lubricant is glycerol dibehenate.

A drug is usually present as active agent in the multiparticulates. The reader is referred to WO 9614058 for examples which is incorporated herein in full by specific reference. Oxycodone is a typical drug for use in the products and processes of this invention.

Therapeutically active agents which may be used in accordance with the present invention include both water soluble and water insoluble drugs. Examples of such therapeutically active agents include antihistamines (e.g. dimenhydrinate, diphenhydramine, chlorpheniramine and dexchlorpheniramine maleate), analgesics (e.g., aspirin, codeine, morphine, dihydromorphone, oxycodone, etc) non-steroidal anti-inflammatory agents (e.g. naproxen, diclofenac, indomethacin, ibruprofen, sulindac), anti-emetics (e.g. metoclopramide, methylnaltrexone), anti-epileptics (e.g., phenyloin, meprobamate and nitrazepam), vasodilators (e.g. nifedipine, papaverine, diltiazem and nicardipine), anti-tussive agents and expectorants (e.g., codeine phosphate), anti-asthmatics (e.g. theophylline), antacids, anti-spasmodics (e.g. atropine, scopolamine), antidiabetics (e.g. insulin), diuretics (e.g. ethacrynic acid, bendrofluthiazide), anti-hypotensives (e.g., propranolol, clonidine), antihypertensives (e.g. clonidine, methyldopa), bronchodilators (e.g. albuterol), steroids (e.g., hydrocortisone, triamcinolone, prednisone), antibiotics (e.g., tetracycline), antihemorrhoidals, hypnotics, psychotropics, antidiarrheals, mucolytics, sedatives, decongestants, laxatives, vitamins, stimulants (including appetite suppressants such as phenylpropanolamine), as well as salts, hydrates, and solvates of the same.

In embodiments of the invention directed to opioid analgesics, the opioid analgesics used in accordance with the present invention include alfentanil, allylprodine, alphaprodine, anileridine, benzylmorphine, bezitramide, buprenorphine, butorphanol, clonitazene, codeine, cyclazocine, desomorphine, dextromoramide, dezocine, diampromide, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene fentanyl, heroin, hydrocodone, hydromorphone, hydroxypethidine, isomethadone, ketobemidone, levallorphan, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propiram, propoxyphene, sufentanil, tramadol, tilidine, salts thereof, mixtures of any of the foregoing, mixed mu-agonists/antagonists, mu-antagonist combinations, and the like. The opioid analgesic may be in the form of the free base, or in the form of a pharmaceutically acceptable salt, or in the form of a pharmaceutically acceptable complex.

In certain preferred embodiments, the opioid analgesic is selected from morphine, codeine, hydromorphone, hydrocodone, oxycodone, dihydrocodeine, dihydromorphine, oxymorphone, tramadol or mixtures thereof.

In one preferred embodiment the sustained-release opioid oral dosage form of the present invention includes hydromorphone as the therapeutically active ingredient in an amount from about 4 to about 64 mg hydromorphone hydrochloride. Alternatively, the dosage form may contain molar equivalent amounts of other hydromorphone salts or of the hydromorphone base. In other preferred embodiments where the opioid analgesic is other than hydromorphone, the dosage form contains an appropriate amount to provide a substantially equivalent therapeutic effect. For example, when the opioid analgesic comprises morphine, the sustained-release oral dosage forms of the present invention include from about 5 mg to about 800 mg morphine, by weight (based on morphine sulfate). When the opioid analgesic comprises oxycodone, the sustained-release oral dosage forms of the present invention include from about 5 mg to about 400 mg oxycodone. When the opioid analgesic is tramadol, the sustained-release oral dosage forms of the invention include from about 50 mg to about 800 mg tramadol by weight, based on the hydrochloride salt.

The sustained-release dosage forms of the present invention generally achieve and maintain therapeutic levels substantially without significant increases in the intensity and/or degree of concurrent side effects, such as nausea, vomiting or drowsiness, which are often associated with high blood levels of opioid analgesics. There is also evidence to suggest that the use of the present dosage forms leads to a reduced risk of drug addiction.

In the present invention, the oral opioid analgesics have been formulated to provide for an increased duration of analgesic. Surprisingly, these formulations, at comparable daily dosages of conventional immediate-release drug, are associated with a lower incidence in severity of adverse drug reactions and can also be administered at a lower daily dose than conventional oral medication while maintaining pain control.

When the therapeutically active agent included in the dosage forms of the present invention is an opioid analgesic, the dosage form may further include one or more additional which may or may not act synergistically with the opioid analgesics of the present invention. Examples of such additional therapeutically active agents include non-steroidial anti-inflammatory agents, including ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamidic acid, meclofenamic acid, flufenamic acid, niflumic acid tolfenamic acid, diflurisal, flufenisal, piroxicam, sudoxicam or isoxicam, and the like. Other suitable additional drugs which may be included in the dosage forms of the present invention include acetaminophen, aspirin, salicylate-derived analgesics and antipyretics or salts thereof, and other non-opioid analgesics.

The additional (non-opioid) therapeutically active agent may be included in controlled release form or in immediate release form. The additional drug may be incorporated into the controlled release matrix along with the opioid; incorporated as a separated controlled release layer or immediate release layer; or may be incorporated as a powder, granulation, etc, in a gelatin capsule with the extrudates of the present invention.

Suitable percentage amounts for the preferred ingredients are given in the following table, based on the total weight of the specified ingredients:

|  | typical range | preferred range | more preferred range | most preferred range |
|---|---|---|---|---|
| water insoluble neutral poly(ethyl acrylate, methyl methacrylate) copolymer | 5 to 66 | 15 to 50 | 20 to 45 | 25 to 45 |
| active agent* | up to 60 | 5 to 55 | 5 to 50 | 10 to 45 |
| water insoluble ammonium methacrylate copolymer | 0 to 85 | 5 to 75 | 5 to 60 | 5 to 45 |
| plasticiser | 0 to 30 | 0 to 25 | 3 to 25 | 3 to 20 |
| lubricant | 0 to 25 | 0 to 25 | 0 to 20 | 0 to 15 |

*the amount of active agent can be 0% in placebo formulations for trials or development work Other additives may also be employed to produce multiparticulates within a set of predetermined specifications. Bulking agents for example lactose, microcrystalline cellulose and calcium phosphate, are widely used pharmaceutical excipients and can be used in the present invention to modify the release rates and/or total release. Other release modifying agents may also be considered to modulate the release rate and/or enhance total release.

The ingredients are blended, and melt extruded. Details of such procedures are given in WO 9614058 incorporated herein in full by specific reference.

For the present invention, we prefer to employ a twin screw extruder. In some embodiments the raw material is fed, as a powder blend, by a feeder, into the first segment of an extruder barrel preferably at relatively low temperature (for example 10-20° C.) to ensure a constant flow of material to the high temperature barrels. The feeder provides a uniform current of the material to the extruder. Consistency is desirable as irregular and variable feeding rates can produce multiparticulates with various physical properties, such as density and porosity.

In other embodiments, for example when using an aqueous dispersion of a polymer, e.g. Eudragit NE 30 D or Eudragit NE 40 D, the raw material may first be wet granulated and dried, and then fed as dried granules or powder to the extruder.

The preferred extruder is designed with twin screws, which may have co-rotating or counter-rotating screws, for the tasks of conveying, blending and compressing the blend as well as providing mechanical energy. The extruder will be equipped with heating means and cooling means as required. The screws which perform a significant part of this melt extrusion process are built of different smaller elements. The mixing and kneading process can be significantly altered by changing the type, length and configuration of the screws elements. Short residence times and moderate to low shear forces contribute to safe processing and stable product even with heat sensitive drugs.

Screw rotating speeds may play a part in the quality of the multiparticulates produced. High rotation speeds without appropriate compensation of the feed rate may produce high porosity multiparticulates with a variable drug release rate. On the other hand slow screw rotation would induce unnecessary long residence times. A vacuum connected to the extruder barrel is desirable to remove trapped air and residual moisture from within the plastified material and thus produce dense multiparticulates ideally of low porosity.

The extrusion head is typically designed to produce multiple strands of fixed diameter, for example 1.0 mm. The number, shape and diameter of the orifices can be changed to suit a predetermined specification.

In addition to the screw speed, the other main influential parameters are the screw torque, individual barrel temperature, and extrusion head pressure and temperature.

As it emerges under pressure as a fluid mix from the orifices of the die-head of the extruder, the mix is cut. By appropriate optimisation of the conditions, as well as generally cylindrical multiparticulates, it is readily possible to obtain spherical or substantially spherical, ellipsoidal or disc shaped multiparticulates.

The multiparticulates may be divided into unit doses such that each individual unit dose includes a dose of drug for administration to a mammal, preferably a human patient.

For the preferred drug, oxycodone or salt thereof, preferably the hydrochloride, a suitable dose of the active agent is 5 to 400 mg, especially 5 mg, 10 mg, 20 mg, 30 mg, 40 mg, 60 mg, 80 mg, 120 mg or 160 mg unit dosages. In this respect, a unit dose contains an effective amount of the therapeutically active agent to produce pain relief and/or analgesia to the patient. The dose of oxycodone administered to a patient will vary due to numerous factors, including the weight of the patient, tolerance, the severity of the pain, the metabolic status and the nature of any other therapeutic agents being administered.

The resultant multiparticulates can be employed as a fill in a capsule. Thus, the present invention provides a capsule suited for once or twice a day dosing. Other dosage forms of the controlled release formulation can be provided.

In one preferred embodiment, the multiparticulates are filled into gelatin capsules each containing a unit dose. The fill weight in the capsule is preferably in the range 80 to 500 mg, more preferably 120 to 500 mg. In a variation of this invention, the unit doses of multiparticulates may be incorporated into other solid pharmaceutical dosage formulations, for example using compression or shaping or forming into tablets, or by forming the extruded product into the form of a suppository.

The preferred capsules or other unit dose forms of this invention preferably are designed for administration at intervals of about 12 or 24 hours.

A preferred drug for inclusion in the multiparticulates is oxycodone or a salt thereof, preferably the hydrochloride. A unit dose form suitable for 12-hourly dosing then suitably has an oxycodone dissolution rate in vitro, when measured by the USP Paddle Method (see the U.S. Pharmacopoeia XXII 1990) at 100 rpm in 900 ml aqueous buffer (pH between 1.6 and 7.2) at 37° C. of between 12.5 and 42.5% (by wt) oxycodone released after 1 hour, between 25 and 56% (by wt) oxycodone released after 2 hours, between 45 and 75% (by wt) oxycodone released after 4 hours and between 55 and 85% (by wt) oxycodone released after 6 hours. Furthermore, we prefer that the peak plasma level of oxycodone obtained in vivo occurs between 2 and 4.5 hours after administration of the dosage form.

More information on desirable characteristics for such oxycodone formulations is given in WO 9310765 which is incorporated herein in full by specific reference.

As an alternative, the capsules or other unit dose forms of this invention are designed for administration at intervals of about 24 hours. To this end, the unit dose form suitably has an oxycodone dissolution rate in vitro, when measured by the USP Basket Method at 100 rpm in 900 ml aqueous buffer at a pH between 1.6 and 7.2 at 37° C. of from 0% to about 40% at 1 hour, from about 8% to about 70% at 4 hours, from about 20% to about 80% at 8 hours, from about 30% to about 95% at 12 hours, from about 35% to about 95% at 18 hours, and greater than about 50% at 24 hours. Furthermore, we prefer that the peak plasma level of oxycodone obtained in vivo is reached at about 2 hours to about 17 hours after administration at steady state of the dosage form.

More information on desirable characteristics for such oxycodone formulations is given in WO 02087512 which is incorporated herein in full by specific reference.

In a variation, the present invention provides unit doses which contain an opioid and an opioid antagonist effective to prevent tampering. In this respect, reference is made to WO 0313433 which is incorporated herein in full by specific reference. In particular, the unit dose can contain oxycodone and naltrexone.

To this ends the present invention provides melt extruded multiparticulates of an opioid such as oxycodone, and melt extruded multiparticulates of an opioid antagonist such as naltrexone. In a preferred formulation antagonist multiparticulates do not release the antagonist on conventional administration, and for example have a non-release coating. Both populations of opioid and opioid antagonist are preferably visually and physically identical.

An important aspect of this invention is a capsule with a unit dose fill of less than 500 mg, comprising up to about 350 mg of oxycodone multiparticulates, and up to about 200 mg of tamper-proof oxycodone antagonist multiparticulates. For example, there can be 120 to 300 mg of oxycodone multiparticulates, and 125 to 175 mg of tamper-proof oxycodone antagonist multiparticulates.

SUMMARY OF THE DRAWINGS

Reference is made in the following experimental section to the accompanying drawings, in which.

EXAMPLES OF THE INVENTION

Figure 1:
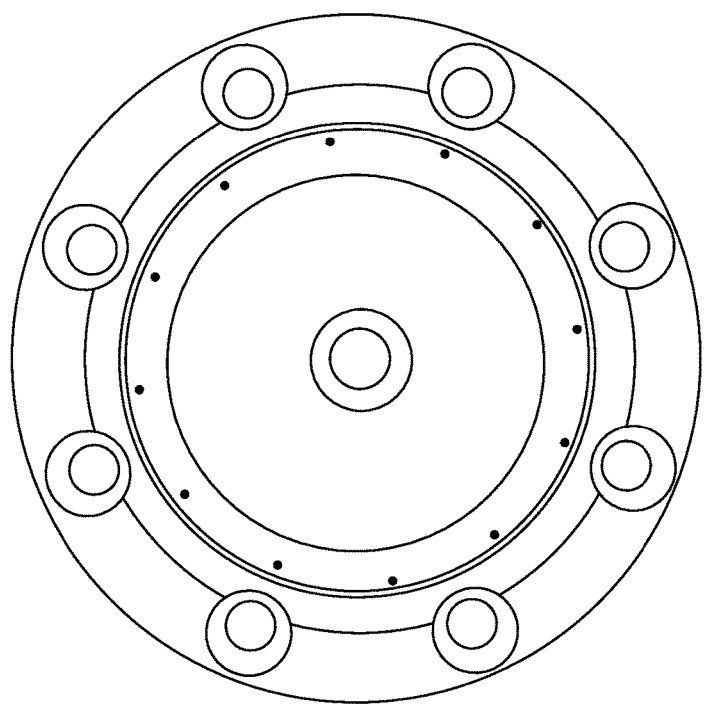
FIG. 1 shows the die-head of a melt extruder.
Figure 2:
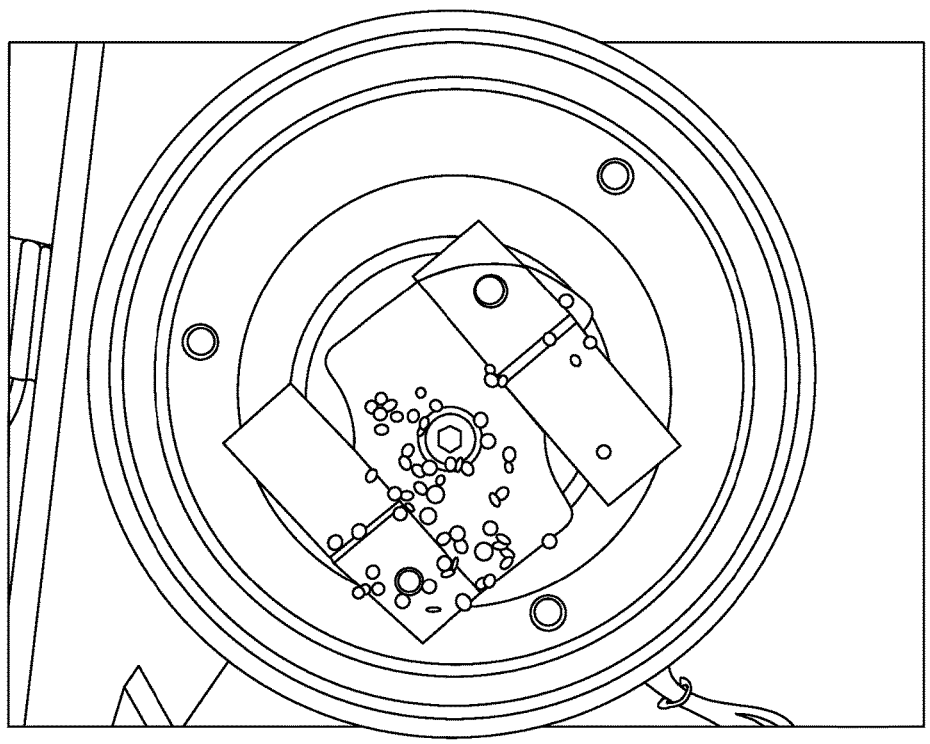
FIG. 2 shows a rotary cutter for use with the die-head of FIG. 1.

In accordance with the novel cutting procedure of the present invention, extrudate emerges from the twelve orifices of the die-head shown in FIG. 1 of a Leistritz Micro 18 extruder. A rotary cutter with two blades, as shown in FIG. 2, is used to cut the extruded mix as it emerges under pressure and still molten from the orifices of the die-plate. The blades sweep over the surface of the die-head to pass the orifices. As the cut extrudate multiparticulates expand and cool, they tend to form rounded surfaces.

The following formulations were employed.

| Material | Examples (% w/w) | | |
| --- | --- | --- | --- |
|  | Example 1 | Example 2 | Example 3 |
| Lactose anhydrous | 25.0 | 8.23 | 10.0 |
| Eudragit RS PO | 56.25 | 74.90 | 37.0 |
| Stearyl alcohol | 6.25 |  | 10.0 |
| Stearic Acid | 12.5 |  | 6.0 |
| Eudragit NE 40 D |  |  | 37.0 |
| Triethyl citrate |  | 8.23 |  |
| PEG 6000 |  | 4.94 |  |
| Magnesium Stearate |  | 3.70 |  |
| Total | 100 | 100 | 100 |
| Comment | Surface cutting Successful good | Surface cutting Successful very good | Surface cutting Successful very good |

Figure 3:
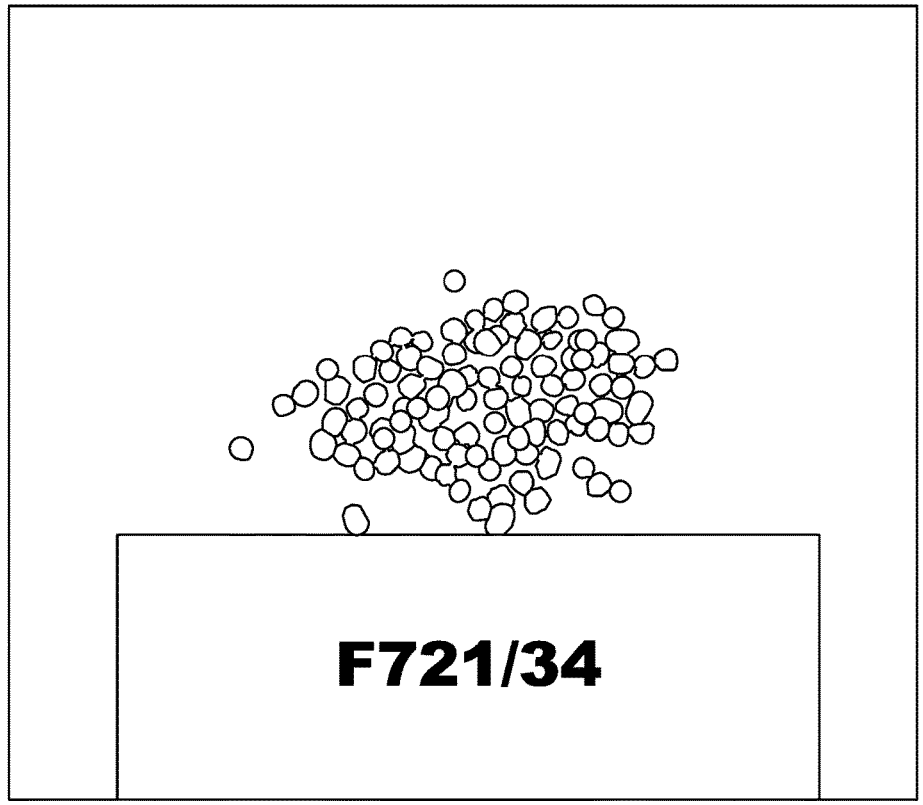
FIGS. 3 to 5 show the products of Example 1, Example 2 and Example 3, respectively.
Figure 4:
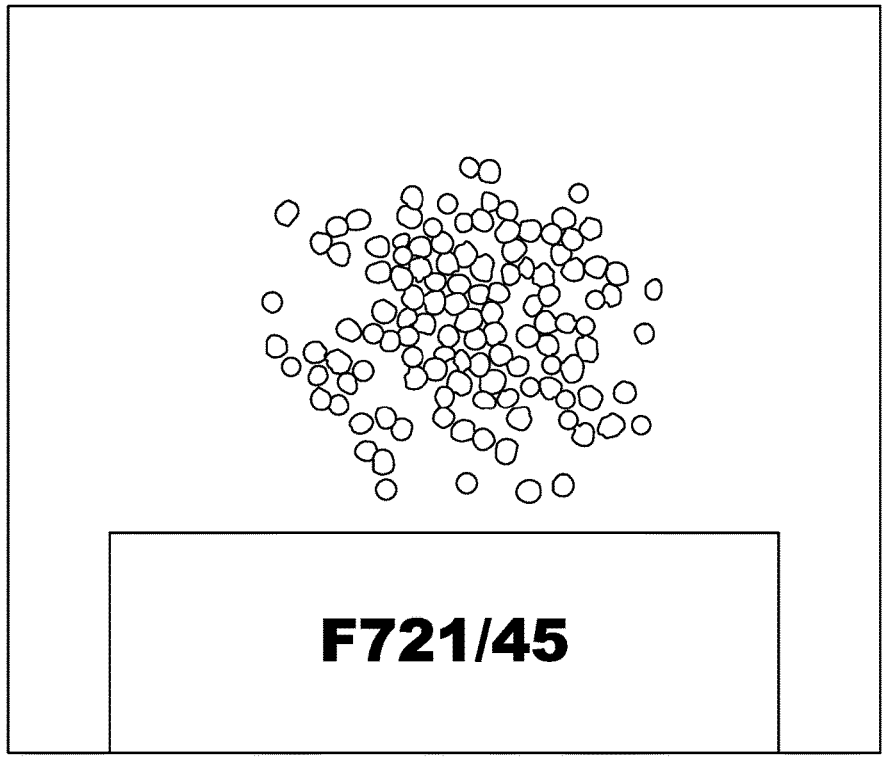
Figure 5:
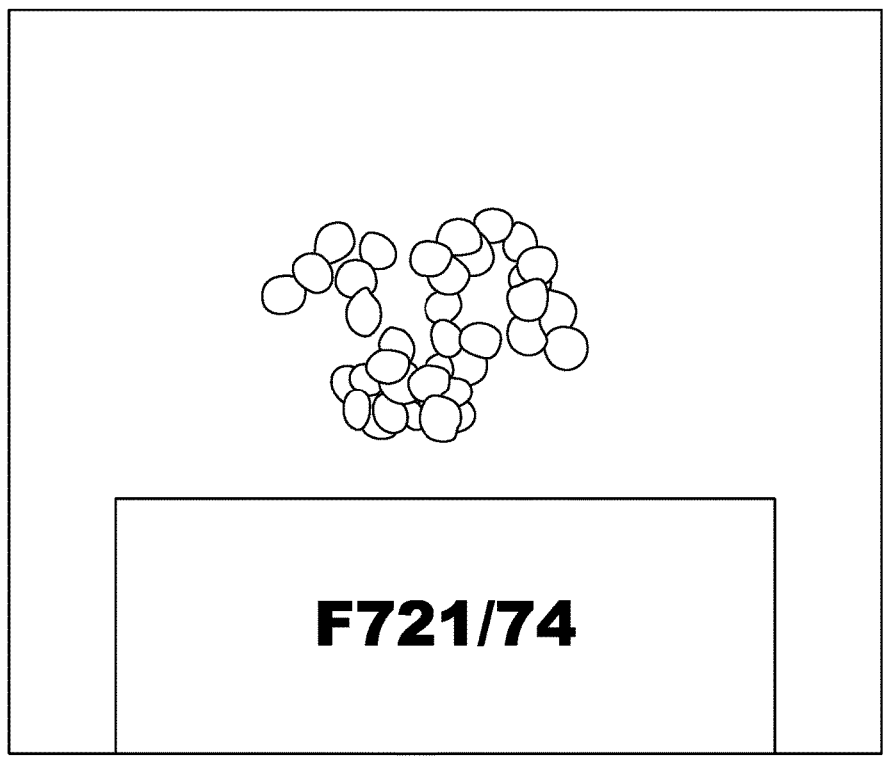

By appropriate adjustment of the conditions, there was no problem to obtain near-spherical multiparticulates (see FIGS. 3 to 5).

The invention claimed is:

1. A process for preparing a plurality of controlled release, spherical or substantially spherical multiparticulates, comprising preparing a controlled release pharmaceutical extrudate using a melt extruder,
   wherein the melt extruder comprises a die-head supporting a die-plate in which orifices are located,
   and a cutter adjacent to the die-head,
   cutting the extrudate as it emerges under pressure and still molten or softened from the orifices of the die-plate, directing a stream of air of reduced temperature into the region of the surface of the die-head during cutting, and wherein the rate of extrusion and the speed of the cutter blade are adjusted to give directly said plurality of spherical or substantially spherical shaped multiparticulates.

2. The process according to claim 1, wherein the cutter is a rotary cutter with two diametrically opposed blades.

3. A process for preparing a plurality of controlled release, spherical or substantially spherical shaped multiparticulates, which process comprises
   providing a melt extruder comprising a die-head supporting a die-plate in which orifices are located, and a cutter adjacent to the die-head,
   feeding a mix through the extruder, cutting the extrudate as it emerges under pressure and still molten or softened from the orifices of the die-plate, directing a stream of air of reduced temperature into the region of the surface of the die-head during cutting, and adjusting the rate of extrusion and the speed of the cutter blade to give directly said plurality of spherical or substantially spherical shaped multiparticulates.

4. The process of claim 1, wherein an outer surface of the die-head is coated with a non-stick material.

5. A process for preparing a plurality of controlled release spherical or substantially spherical multiparticulates comprising a neutral poly(ethyl acrylate, methyl methacrylate) copolymer, sad process comprising using a melt extruder, wherein the melt extruder comprises a die-head supporting a die-plate in which orifices are located, and a cutter adjacent to the die-head, cutting the extrudate comprising the neutral poly(ethyl acrylate, methyl methacrylate) copolymer as it emerges under pressure and still molten or softened from the orifices of the die-plate, directing a stream of it of reduced temperature into the region of the die-head during cutting, and adjusting the rate of extrusion and the speed of the cutter blade to give directly said plurality of spherical or substantially spherical multiparticulates.

\* \* \* \* \*